(12) United States Patent
Yu

(10) Patent No.: US 11,459,356 B2
(45) Date of Patent: Oct. 4, 2022

(54) NEURONAL NICOTINIC ACETYLCHOLINE RECEPTOR-TARGETING POLYPEPTIDE AND USE THEREOF

(71) Applicant: Mingjia Yu, Foshan (CN)

(72) Inventor: Mingjia Yu, Foshan (CN)

(73) Assignee: Mingjia Yu, Foshan (CN)

( * ) Notice: Subject to any disclaimer, the term of this patent is extended or adjusted under 35 U.S.C. 154(b) by 0 days.

(21) Appl. No.: 17/329,191

(22) Filed: May 25, 2021

(65) Prior Publication Data
US 2022/0242909 A1    Aug. 4, 2022

(30) Foreign Application Priority Data

Jan. 29, 2021   (CN) .......................... 202110129653.X

(51) Int. Cl.
*C07K 7/08*   (2006.01)
*A61K 38/00*   (2006.01)

(52) U.S. Cl.
CPC ................ *C07K 7/08* (2013.01); *A61K 38/00* (2013.01)

(58) Field of Classification Search
None
See application file for complete search history.

(56) References Cited

U.S. PATENT DOCUMENTS

2016/0122388 A1\*  5/2016  McIntosh ............... A61P 25/00
514/21.5

\* cited by examiner

*Primary Examiner* — Christina Bradley
(74) *Attorney, Agent, or Firm* — Bayramoglu Law Offices LLC

(57) ABSTRACT

A neuronal nicotinic acetylcholine receptor-targeting polypeptide and the use thereof are disclosed. The polypeptide has an amino acid sequence of SEQ ID NO:1, and includes four cysteine residues, $Cys^2$, $Cys^3$, $Cys^7$, and $Cys^{13}$, that can form two disulfide bonds. Molecular docking simulation illustrated its capacity to target a and a subunits of nAChR and the stable structure of resultant nAChR_BP-nAChR complex. In addition, effect of the polypeptide on calcium response of nAChR-overexpressing CN21 cells revealed that the polypeptide was capable of significantly inhibiting nAChRs. Accordingly, the nAChR-targeting polypeptide nAChR_BP is a promising nAChR-targeting drug.

4 Claims, 4 Drawing Sheets

Specification includes a Sequence Listing.

NEURONAL NICOTINIC ACETYLCHOLINE RECEPTOR-TARGETING POLYPEPTIDE AND USE THEREOF

CROSS REFERENCE TO THE RELATED APPLICATIONS

This application is based upon and claims priority to Chinese Patent Application No. 202110129653.X, filed on Jan. 29, 2021, the entire contents of which are incorporated herein by reference.

TECHNICAL FILED

The present invention relates to the technical field of biomedicine, and particularly relates to a neuronal nicotinic acetylcholine receptor-targeting polypeptide and the use thereof.

BACKGROUND

Nicotinic acetylcholine receptors (nAChRs) are members of acetylcholine-gated cation channels and major excitatory neurotransmitter receptors formed in muscle and nerve in the peripheral nervous system. The pathogenic effects of nAChRs have been identified in many diseases, involving mechanisms ranging from mutation to autoimmune response, cells ranging from myocytes, neurons to keratinocytes, and diseases such as muscle weakness, epilepsy, neurodegenerative diseases, mental illness and nicotine addiction. The finding that nAChRs are involved in the diseases has led to novel studies, such as the development of therapeutic agonists or antagonists for specific nAChR subtypes, and the use of cloned nAChR subunits as possible immunotherapy drugs.

Polypeptides have been promising approach of drug development for their highly specific targeting capacity and safety. Currently, predicting the binding mode and affinity between a polypeptide and a target protein through molecular simulation and docking has become an important technology in the field of computer-aided drug research.

There is an urgent need to study and develop compounds that can specifically target the nicotinic acetylcholine receptors, which provides a basis for the development of new drugs for the treatment of human-related diseases in the future.

SUMMARY

One object of the present invention is, in order to address the prior art deficiencies, to provide a novel polypeptide (named nAChR_BP) that targets neuronal nicotinic acetylcholine receptor.

The polypeptide is featured by its capacity of targeting a and a subunits of nAChR and the stable structure of resultant nAChR_BP-nAChR complex.

A second object of the present invention is, in order to address the prior art deficiencies, to provide the use of the polypeptide.

Technical solutions for realizing the objects comprise the polypeptide, which has an amino acid sequence of SEQ ID NO: 1.

Specifically, the polypeptide comprises a first disulfide bond between Cys-2 and Cys-13 (i.e., between the cysteine residue at the second position and the cysteine residue at the thirteenth position), and a second disulfide bond between Cys-3 and Cys-7 (i.e., between the cysteine residue at the third position and the cysteine residue at the seventh position).

The polypeptide (nAChR_BP) as described above interacts with a and a subunits of nAChR.

The invention also involves the use of the above-mentioned polypeptide (nAChR_BP).

Specifically, one aspect of the use is to provide a composition for the treatment of nAChR-related diseases, wherein the composition comprises an effective amount of the polypeptide (nAChR_BP) as an active ingredient and a pharmaceutically acceptable carrier.

Another aspect is to provide a method for treating nAChR-related diseases, wherein the method comprises administering to a subject in need thereof an effective amount of the polypeptide or a composition comprising the polypeptide as an active ingredient.

The diseases as mentioned above comprise muscle weakness, epilepsy, neurodegenerative diseases, mental diseases, and nicotine addiction, and facial and body wrinkles caused by muscle tension.

Beneficial Effects of the Present Invention

A novel polypeptide named nAChR_BP has been developed based on the polypeptide chain folding and molecular docking technology. The polypeptide (nAChR_BP) comprises four cysteine residues, $Cys^2$, $Cys^3$, $Cys^7$, and $Cys^{13}$, that can form two disulfide bonds. Molecular docking simulation illustrated its capacity to target a and a subunits of nAChR and the stable structure of resultant nAChR_BP-nAChR complex. In addition, effect of the polypeptide on calcium response of nAChR-overexpressing CN21 cells revealed that the polypeptide was capable of significantly inhibiting nAChRs. Accordingly, the present invention provides a nAChR-targeting polypeptide nAChR_BP, which is a promising nAChR-targeting drug with broad application prospects.

In view of the above, another aspect is to provide a method for inhibiting nAChR, comprising administering to a subject in need thereof an effective amount of the polypeptide or a composition comprising the polypeptide as an active ingredient.

BRIEF DESCRIPTION OF THE DRAWINGS

The drawings are provided to further illustrate the present invention rather than limit the present invention.

FIG. 0.5 is a diagram showing the calcium response of nAChR-overexpressing CN21 cells pre-incubated with different concentrations of the polypeptide nAChR_BP.

DETAILED DESCRIPTION OF THE EMBODIMENTS

The present invention will be further described with the following embodiments and the drawings.

1. Design of Polypeptide nAChR_BP

By comparing and screening the amino acid sequences of various nAChR-blocking molecules using Vector NTI 10.3, distribution of amino acid sequences having nAChR-blocking effect were obtained for lead compound design. The results were edited using BioEdit and thereby the sequence of the polypeptide nAChR_BP was obtained.

2. Prediction of Three-Dimensional Structure of Polypeptide nAChR_BP

Prediction of the three-dimensional structure of the polypeptide nAChR_BP was performed by MODELLER:

(1) BP.ali and pdb_95.pir files were prepared.

(2) We ran command "prf.build ( )" to search for pdb templates of structures similar to the target gene. The output results were stored in the BPout.prf file, wherein the first six lines recorded the relevant parameters of MODELLER to build this file, and the subsequent lines recorded the similar structures detected by "prf.build ( )". Templates with higher similarities and lower E value were selected.

(3) We downloaded the pdb document of the above candidate templates from the pdb template database, and ran command "for ( ) in ( )" to determine the best template.

(4) Command "automodel ( )" was run in the MODELLER window to obtain the protein prediction results.

(5) The result with the lowest DOPE score and the highest GA341 was selected as the best model.

Figure 1A:
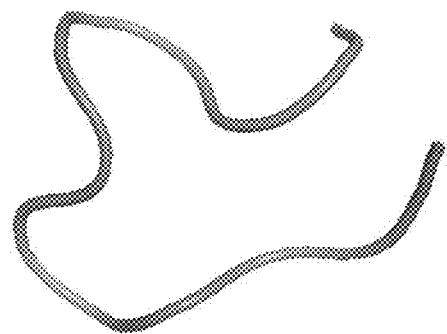
FIG. 1A is a diagram showing a three-dimensional structure of the polypeptide nAChR_BP.
Figure 1B:
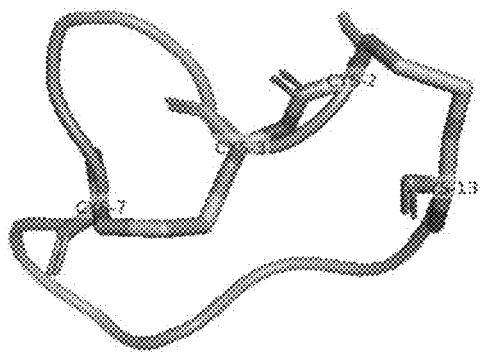
FIG. 1B is another diagram showing the three-dimensional structure of the polypeptide nAChR_BP.
Figure 2A:
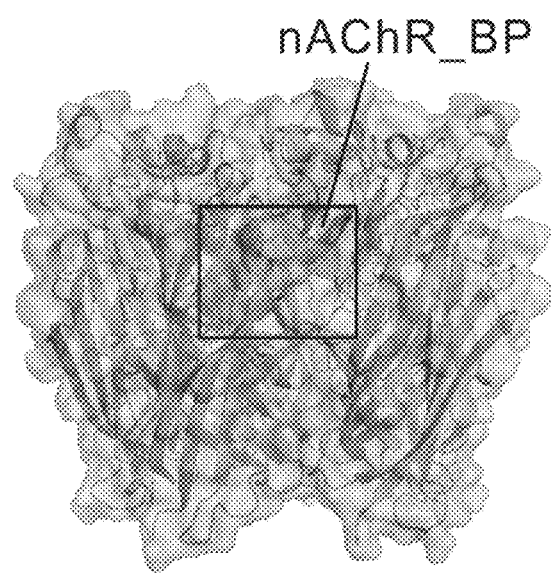
FIG. 2A is a diagram showing the molecular docking between the polypeptide nAChR_BP and nAChR from a side view.
Figure 2B:
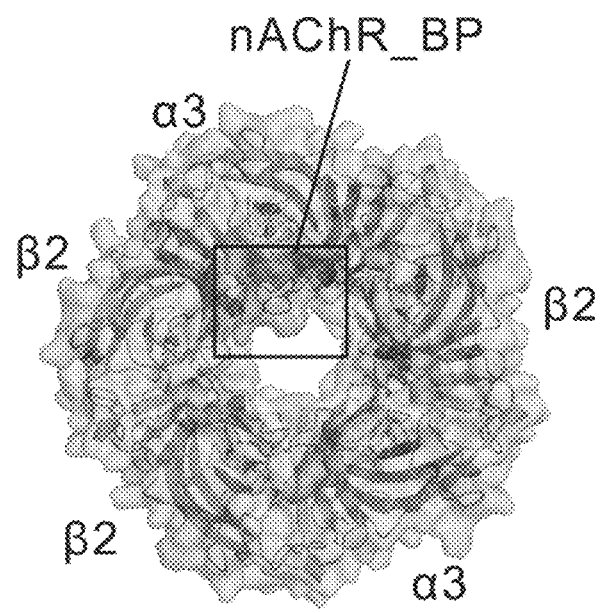
FIG. 2B is a diagram showing the molecular docking between the polypeptide nAChR_BP and nAChR from a top view.
Figure 2C:
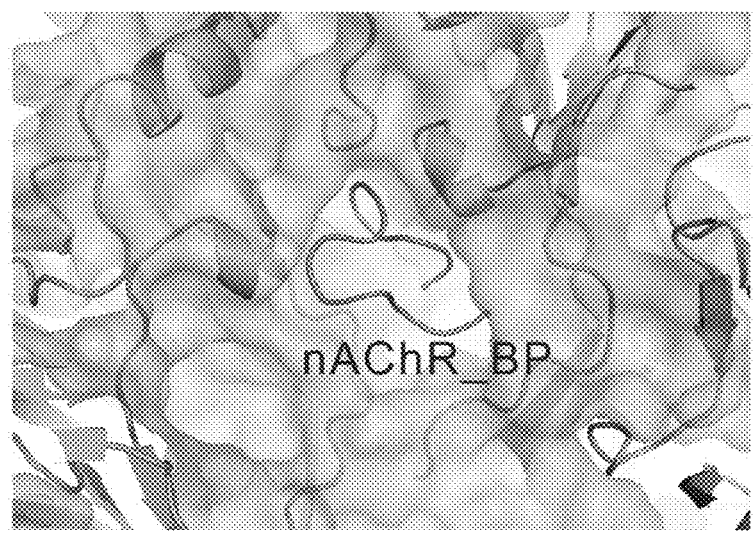
FIG. 2C is a diagram showing the molecular docking between the polypeptide nAChR_BP and nAChR.

(6) The result was opened in PyMOL software to obtain images of the three-dimensional structure of the polypeptide nAChR_BP (see FIGS. 1A-B).

3. Molecular Docking Analysis Between Polypeptide nAChR_BP and Nicotinic Acetylcholine Receptor (nAChR)

Docking analysis was performed by using ZDOCK, a Fast Fourier Transform (FFT)-based, rigid-body protein-protein docking algorithm:

(1) The pdb files of nAChR and the polypeptide nAChR_BP were prepared.

(2) The files of the receptor and the ligand were opened in the same window in Discovery Studio 4.0.

(3) ZDOCK settings: angular step size=15; ZRank=False; clustering of docking conformations (Top poses=2000; RMSD Cutoff=6.0; Interface Cutoff=9.0; Maximum Number of Clusters=60); parallel computing=True.

(4) ZDOCK was run and a resultant model with the highest score was selected.

(5) The docking model was opened in PyMOL software to analyze the active pocket and docking site.

4. Dynamic Simulation Analysis of nAChR_BP-nAChR Complex

Dynamic simulation of nAChR crystal and nAChR_BP-nAChR complex was performed using NAMD and VMD:

(1) We opened the Tk Console in the VMD menu, ran "cd" command to visit the designation folder, ran "mol new filename.pdb" command, and created a psf file using Automatic PSF Builder by calling a top_all27_prot_lipid_na.inp script, loading script information to form a chain and thereby the psf file was created.

(2) A filename.pdb file and a filename.psf file were created, renamed as original.pdb and original.psf. We then used "Add Solvation Box" to solvate the protein (boundary=1.5).

(3) We ran minimization.namd to perform energy minimization, wherein the boundary data was obtained by using findbox.tcl, and a par_a1136_lipid_prot_carb.prm script was also provided. Energy minimization was realized by running command "namd2 +p4 minimize.namd >dummy.out".

(4) A nvt.namd script was provided. Dynamic simulation was performed on the file after energy minimization by running command "namd2 +p8 nvt.namd >dummy.out".

(5) The output results were analyzed to give information such as heating results and dynamic potential energy during the dynamic simulation. We then plotted the RSMD by using RMSDplot, and results were as shown in FIG. 3 and FIG. 4.

Figure 3:
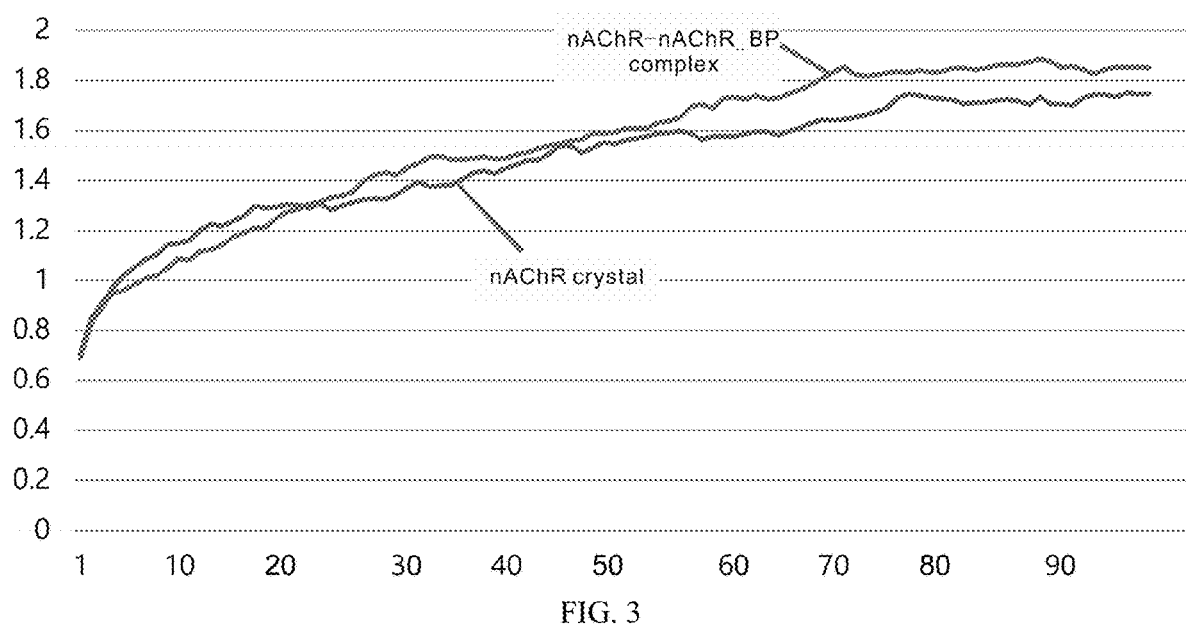
FIG. 3 is a diagram showing the changes in average RMSD of the whole protein by dynamic simulation.

In FIG. 3, the two curves respectively indicate the changes in RMSD of nAChR crystal and nAChR_BP-nAChR complex, which demonstrate the activity of protein backbone during the dynamic simulation.

Figure 4:
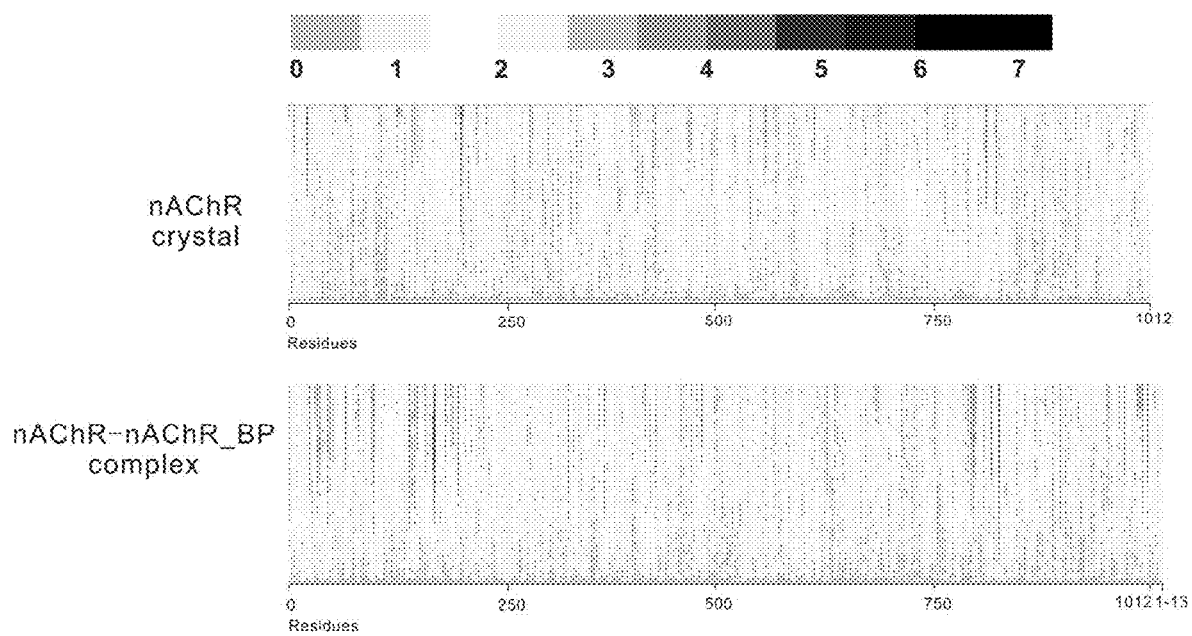
FIG. 4 is a diagram showing the changes in RMSD of each amino acid residue by dynamic simulation.
Figure 5:
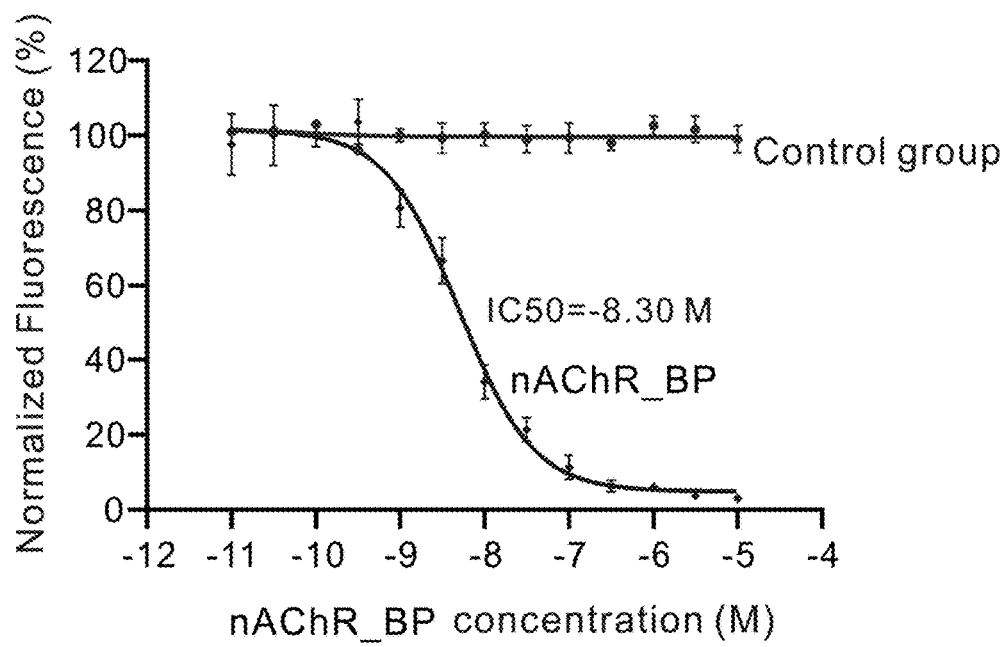

In FIG. 4, the upper section shows the RMSD of each amino acid residue in nAChR crystal and the lower section shows the RMSD of each amino acid residue in nAChR_BP-nAChR complex. The abscissas refer to the positions of the amino acid residues, and the RMSD values were indicated by the color as shown on the scale.

5. Synthesis of Polypeptide nAChR_BP (1) The polypeptide can be synthesized by conventional Fmoc solid-phase peptide synthesis. In this embodiment, the polypeptide was synthesized in a synthesizer by Fmoc solid-phase peptide synthesis, accompany with HATU as coupling reagent. 0.2 mmol Wang resin was added to the reaction column. Generally, 3 eq. amino acid was applied for continuous coupling reaction.

(2) Formation of the first disulfide bond (2a) Deprotection of Cys (Mmt): In a glass reactor equipped with a glass frit, the peptide resin was treated with 2% trifluoroacetic acid (TFA) and dichloromethane (DCM) containing 5% TIS for 10 minutes, and mixed with nitrogen. After filtration, the peptide resin was washed with DCM. The steps of deprotection and washing were repeated for seven times. Finally, the peptide resin was washed with DCM and dimethylformamide (DMF).

(2b) Oxidation of disulfide bond: In a glass reactor equipped with a glass frit, DMF solution with 2eq. N-chlorosuccinimide (NCS) was applied to treat the free mercaptan peptide resin for 30 minutes, and mixed with nitrogen. After filtration, the peptide resin was washed with DCM. The steps of deprotection and washing were repeated for seven times. Finally, the peptide resin was washed with DCM and DMF.

(3) Formation of the second disulfide bond (3a) Deprotection of Cys (Acm): In a glass reactor equipped with a glass frit, the peptide resin collected from Step (2) was treated with frozen 95% (95% TFA+2% TIS+1% EDT+2% $H_2O$) for 120 minutes. After filtration, the filtrate was precipitated with cold diethyl ether, and centrifuged at 4000 rpm, followed by freeze-dry to obtain a white solid powder.

(3b) Oxidation of disulfide bond: Peptide was dissolved in water to a final concentration of 1 mg/mL. The peptide suspension was adjusted to pH 8.0 with ammonium bicarbonate, and the mixture was stirred for 12 hours at room temperature. Then, peptide was precipitated in the tubes containing cold diethyl ether, and purified by HPLC. Finally, the peptide was freeze-dried and stored at −20° C.

6. Inhibitory Activity of Polypeptide nAChR_BP Against nAChR

The bioactivity of polypeptide nAChR_BP was assessed by using C21 human cells expressing human nAChR. The CN21 cells were incubated in 12-well plates one day prior. After 25 hours of incubation, the media were removed and new media containing various concentrations ($10^{-11}$-$10^{-5}$ M) of the polypeptide were added to incubate the cells. Six hours later, concentrations of calcium ion were measured using a kit, such that the activity of nAChR_BP was determined in vitro by assessing the antagonism of the nAChR mediated increase of [Ca2+] in CN21 cells. As show in FIG. 5, the effect of various concentrations of the polypeptide on calcium response of nAChR-overexpressing CN21 cells revealed that the polypeptide was capable of significantly inhibiting nAChRs.

In view of the above, the polypeptide can be used to inhibit nAChR, by administering to a subject in need thereof an effective amount of the polypeptide or a composition comprising the polypeptide as an active ingredient.

Accordingly, the polypeptide disclosed herein may be combined with pharmaceutically acceptable carriers to form therapeutic compositions.

In one embodiment, a composition comprising an effective amount of the polypeptide as an active ingredient and a pharmaceutically acceptable carrier is provided for the treatment of nAChR-related diseases.

In another embodiment, a composition comprising the polypeptide as an active ingredient is provided for inhibiting nAChR.

It should be noted that the above embodiments are only used to illustrate the technical solutions of the present invention, but not to limit the scope of the present invention. Although the present invention has been described in detail with reference to the preferred embodiments, those of ordinary skill in the art should understand that the technical solutions of the present invention can be modified or equivalently replaced without departing from the essence and scope of the technical solutions of the present invention.

What is claimed is:

1. A polypeptide having an amino acid sequence of SEQ ID NO:1, wherein the polypeptide comprises a first disulfide bond between Cys-2 and Cys-13, and a second disulfide bond between Cys-3 and Cys-7.

2. A composition for treating nAChR-related diseases, comprising an effective amount of the polypeptide of claim 1 as an active ingredient and a pharmaceutically acceptable carrier.

3. A method for treating nAChR-related diseases, comprising administering to a subject in need thereof an effective amount of the polypeptide of claim 1, or administering to the subject a composition comprising the polypeptide as an active ingredient.

4. The method of claim 3, wherein the nAChR-related diseases comprise muscle weakness, epilepsy, neurodegenerative diseases, mental diseases, nicotine addiction, and facial and body wrinkles caused by muscle tension.

\* \* \* \* \*

SEQUENCE LISTING

<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: The sequence is synthesized.

<400> SEQUENCE: 1

Ala Cys Cys Leu Phe Asn Cys His Ser Trp Val Gly Cys
1 5 10